(12) United States Patent
Joichi et al.

(10) Patent No.: US 8,791,059 B2
(45) Date of Patent: Jul. 29, 2014

(54) FRAGRANCE COMPOSITIONS

(71) Applicants: Shiseido Company Ltd., Tokyo (JP); Takasago International Corporation, Tokyo (JP)

(72) Inventors: Atushi Joichi, Yokohama (JP); Yasuko Nakamura, Yokohama (JP); Shinichiro Haze, Yokohama (JP); Takahiro Ishikawa, Hiratsuka (JP); Takashi Nishida, Yokohama (JP); Kazutoshi Sakurai, Fujisawa (JP)

(73) Assignees: Shiseido Company, Ltd., Tokyo (JP); Takasago International Corporation, Tokyo (JP)

( * ) Notice: Subject to any disclaimer, the term of this patent is extended or adjusted under 35 U.S.C. 154(b) by 0 days.

(21) Appl. No.: 13/799,317

(22) Filed: Mar. 13, 2013

(65) Prior Publication Data

US 2013/0253076 A1    Sep. 26, 2013

Related U.S. Application Data

(62) Division of application No. 13/202,070, filed as application No. PCT/JP2010/053199 on Mar. 1, 2010, now Pat. No. 8,426,354.

(30) Foreign Application Priority Data

Mar. 6, 2009   (JP) ................. 2009-052790
Dec. 24, 2009  (JP) ................. 2009-292707

(51) Int. Cl.
    *A61Q 13/00* (2006.01)
(52) U.S. Cl.
    USPC ............................................. 512/2
(58) Field of Classification Search
    CPC .......... A61K 8/37; A61K 8/49; C11B 9/0096; C11B 9/003; A61Q 13/00; A61Q 5/00; A61Q 15/00; A61Q 19/00; A61Q 19/10; A61Q 5/02
    USPC ............................................ 512/10
    See application file for complete search history.

(56) References Cited

U.S. PATENT DOCUMENTS

| | | | |
|---|---|---|---|
| 4,594,464 A * | 6/1986 | Boden et al. ................ | 568/592 |
| 5,800,897 A | 9/1998 | Sharma et al. | |
| 7,192,913 B2 | 3/2007 | Clark et al. | |
| 2003/0186399 A1 | 10/2003 | Farbood et al. | |

FOREIGN PATENT DOCUMENTS

| | | |
|---|---|---|
| CH | 604714 A5 | 9/1978 |
| EP | 0211303 A2 | 2/1987 |
| EP | 1424071 A1 | 6/2004 |
| GB | 1557382 A | 12/1979 |
| JP | 03-118348 A | 5/1991 |
| JP | 03-284618 A | 12/1991 |
| JP | 03284618 A * | 12/1991 ............ A61K 7/46 |
| JP | 2006-219413 A | 8/2006 |
| JP | 2007-091663 A | 4/2007 |
| JP | 2008-169334 A | 7/2008 |
| JP | 2008169334 A * | 7/2008 |
| JP | 2008-188868 A | 8/2008 |

OTHER PUBLICATIONS

English Translation of JP 2008-169334 A obtained Jul. 2012 at http://www19.ipdl.inpit.go.jp/PA1/cgi-bin/PA1DETAIL.*
English Translation of JP 03-284618 obtained Aug. 2011 at http://www19.ipdl.inpit.go.jp/PA1/cgi-bin/PA1DETAIL.*
Japanese Office Action dated Jan. 28, 2014 in Japanese Application No. 2009-292707.
Hugo Weenen et al, Sulfur-Containing Volatiles of Durian Fruits (*Durio zibethinus* Murr.), J. Agric. Food Chem., 1996, 44, pp. 3291-3293.
Jennifer M. Ames, "Volatile Surfur Compounds in Yeast Extracts", American Chemical Society Symposium series, 1994, 564, (Sulfur Compounds in Foods), pp. 147-159.
Japan Patent Office Bulletin, Collection of Well-known Prior Arts, Flavors or Fragrances Part III, Fragrances, p, 482, and one page containing English-language translation of a portion of p. 482, (2001).
Indo Motiichi, "<Enlarged and revised edition> Synthetic Flavor, Chemistry and product knowledge" , The Chemical Daily Co., Ltd., Mar. 22, 2005, pp. 675-677, and two pages containing English-language translation of a portion of Motiichi paper.
S. Tamogami et al, "Analysis of the enantiomeric ratios of chiral components in absolute jasmine", Flavor and Fragrance Journal, 2001, pp. 161-163, vol. 16.
Olcay Anac, Gas Chromatographic Analysif of Absolutes and Volatile Oil Isolated from Turkish and Foreign Jasmine Concretes, Flavor and Fragrance Journal, 1986, pp. 115-119, vol. 1.
Akihiko Omata et al, "Volatile Components of TO-YO-RAN Flowers (*Cymbidium fabefi* and *Cymbidium virescens*)", Agric. Biol. Chem., 54(4), 1990, pp. 1029-1033.
Maria Del Mar Caja et al, Online RPLC-GC via TOTAD Method to Isolate (+)-Methyl Epijasmonate from Lemon (*Citrus limon* Burm.). J. Agric. Food Chem., 2008, 56, pp. 5475-5479.
Ritsuo Nishida et al, Isolation and Characterization of Methyl Epijasmonate from Lemon (*Citrus limon*, Burm.), J. Agric. Food Chem., 1984, 32, pp. 1001-1003.
Yoshitaka Ueyama et al, The Volatile Constituents of Shi Mei (*Rosa davurica* Pall.), Flavor and Fragrance Journal, 1990, pp. 115-120, vol. 5.
Supplementary European Search Report dated Jun. 18, 2012 for EP 10748694.
International Search Report mailed Apr. 20, 2010 for PCT/JP2020/053199.
European Search Report for EP 13189047 mailed Jan. 3, 2014.

* cited by examiner

*Primary Examiner* — Ling Choi
*Assistant Examiner* — Lanee Reuther
(74) *Attorney, Agent, or Firm* — Holtz Holtz Goodman & Chick PC

(57) ABSTRACT

A rose-like fragrance composition including methyl epijasmonate, provided that a natural jasmine fragrance containing methyl epijasmonate is excluded. The rose-like fragrance composition can also include 2-isopropyl-4-methyl thiazole.

11 Claims, No Drawings

FRAGRANCE COMPOSITIONS

CROSS REFERENCE TO RELATED APPLICATIONS

This application is a divisional application of application Ser. No. 13/202,070 filed Aug. 17, 2011 (U.S. Pat. No. 8,426,354), which is the United States national phase application of International application PCT/JP2010/053199 filed Mar. 1, 2010. The entire contents of each of Ser. No. 13/202,070 and PCT/JP2010/053199 are incorporated by reference herein.

TECHNICAL FIELD

The present invention relates to a fragrance composition, and more particularly, to a fragrance composition having an excellent rose-like aroma.

BACKGROUND ART

A rose aroma is an excellent aroma appreciated as "flower of flowers" and has been used in a variety of forms for thousands of years. From old times, a natural rose aroma has been considered to be the best as the rose aroma, and in order to obtain the most typical and sophisticated rose aroma, a natural rose essential oil extracted from natural rose (petal) has been blended for use in cosmetic compositions and the like. The natural rose essential oil has been used not from very old days only for enjoying the aroma as described above but also for drugs or in ceremonies and the like. The natural rose essential oil was extracted, in the ancient times, from a petal of the species *Rosa damascena* or *Rosa centifolia* or the like and is a main component of the so-called "ancient rose-like aroma." The aroma remains unchanged from those days until now and is a strong aroma with some sticky sweetness. The aroma is exactly what it was in the old days.

On the other hand, the number of rose breeds has exploded up to about twenty thousand or more by subsequent natural crossings of original species and many artificial crossings for producing species excellent as ornamental rose after the 19th century, based on the original species *Rosa ciamascena* or *Rosa centifolia* or the like as described above, and this trend provides significant changes in rose aromas. As the so-called modern rose, for example, tea rose and hybrid tea rose are known. Recently, a flower having blue color as a keynote developed by genetic engineering, blue moon that is called blue type HT rose, and the like have become popular. Aroma components of rose include geraniol, citronellol, rose oxide, 2-phenylethyl alcohol, and the like, and a few hundreds of fragrance components have been clarified by analyses of aroma.

In addition, with regard to a rose-like blended fragrance, it is known that 2-methyl thiazole is blended in a rose-like blended fragrance of *Rose ciamascena* or *centifolia* type (see Patent Literature 1).

"2-Isopropyl-4-methyl thiazole" used in the present invention is known to be contained in tea, durian, which is a tropical fruit, and yeast extract (see Non Patent Literatures 1 and 2) in nature and has been used as a flavor component in meat- and tropical fruit-like flavor compositions.

However, because of the aroma character of the compound, usability of the compound as an aroma component for fragrance has not been known.

Of course, it has not been reported that 2-isopropyl-4-methyl thiazole was found in a rose aroma component.

With regard to the rose-like blended fragrance, it is known that jasmine oil is blended in a rose-like blended fragrance of *Rosa centifolia* type (see Non Patent Literature 3).

"Methyl epijasmonate" used in the present invention is known to be contained as an aroma component of jasmine absolute (see Non Patent Literatures 4 to 6) or orchid (see Non Patent Literature 7) or in a fruit such as citrus (lemon) (see Non Patent Literatures 8 and 9) in nature, and has been used as a fragrance or a fragrance mainly for imparting a jasmine-like aroma. For example, methyl epijasmonate is known to be used as an active ingredient of an oriental orchid-like fragrance composition (see Patent Literature 2).

However, because of the aroma character of the compound, usability of the compound as a rose-like aroma component has not been known. Of course, it has not been reported that methyl epijasmonate was found in a rose aroma component.

It should be noted that 'methyl jasmonate,' which is a stereoisomer of methyl epijasmonate, has been reported as an aroma component of Chinese rose, but it has not been reported that the compound, i.e., "methyl epijasmonate" was found in a rose aroma component (see Non Patent Literature 10).

CITATION LIST

Patent Literature Document

[Patent Literature Document 1] JP 2006-219413 A
[Patent Literature Document 2] JP 03-284618 A

Non Patent Literature Document

[Non Patent Literature Document 1] Hugo Weenen et al., J. Agric. Food Chem., 1996, 44, p. 3291-3293
[Non Patent Literature Document 2] Jennifer M. Ames, American Chemical Society Symposium series, 1994, 564 (SULFUR COMPOUNDS IN FOODS), p. 147-159
[Non Patent Literature Document 3] Japan Patent Office bulletin, Collection of Well-known Prior Arts, Flavors or Fragrances Part III, Fragrances, P482
[Non Patent Literature Document 4] "<Enlarged and revised edition> Synthetic Flavor, Chemistry and product knowledge" written by Indo Motiichi, The Chemical Daily, Co., Ltd., Mar. 22, 2005, p. 675-677
[Non Patent Literature Document 5] FLAVOR AND FRAGRANCE JOURNAL, VOL. 16, 161-163 (2001)
[Non Patent Literature Document 6] FLAVOR AND FRAGRANCE JOURNAL, VOL. 1, 115-119 (1986)
[Non Patent Literature Document 7] Agric. Biol. Chem., 54(4), 1029-1033, (1990)
[Non Patent Literature Document 8] J. Agric. Food Chem., 2008, 56, 5475-5479
[Non Patent Literature Document 9] J. Agric. Food Chem., 1984, 32, 1001-1003
[Non Patent Literature Document 10] FLAVOR AND FRAGRANCE JOURNAL, VOL. 5, 115-120 (1990)

SUMMARY OF INVENTION

Technical Problem

Therefore, even if components which have conventionally been known to have rose aromas are combined, it is difficult to reproduce a fresh and rich aroma of rose, and a method of realizing the reproduction has been required. Accordingly, an object of the present invention is to provide a fragrance composition having a natural rose aroma with freshness, sweetness, and softness.

Moreover, it is difficult to reproduce an excellent rose aroma with naturalness, freshness, and richness, and a method of realizing the reproduction has been required. Accordingly, an object of the present invention is to provide a fragrance composition having an excellent rose-like aroma with naturalness, freshness, and richness.

Solution to Problem

The inventors of the present invention have made intensive studies to solve the above-mentioned problems of the conventional technologies. As a result, the inventors have found that when 2-isopropyl-4-methyl thiazole, which has not been elucidated as an aroma component in a rose essential oil, is added alone or in combination with rose oxide, a natural rose aroma with freshness, sweetness, and softness can be created, and the aroma evokes blue type rose.

That is, the present invention includes the following.
(1) A fragrance composition, having added thereto 2-isopropyl-4-methyl thiazole.
(2) A fragrance composition according to the item (1), in which the fragrance composition has a rose-like aroma.
(3) A fragrance composition according to the item (1) or (2), in which the fragrance composition has 2-isopropyl-4-methyl thizole and rose oxide added thereto.
(4) A fragrance composition according to any one of the items (1) to (3), in which 2-isopropyl-4-methyl thiazole is added to the fragrance composition at a concentration of 0.1 ppm to 5,000 ppm.
(5) A fragrance composition according to any one of the items (1) to (4), in which the mix ratio of 2-isopropyl-4-methyl thiazole to rose oxide in the fragrance composition is in the range of 1:1 to 1:250.
(6) A method of imparting an aroma to a fragrance composition, the method including adding 2-isopropyl-4-methyl thiazole to a base fragrance composition having a rose-like aroma as a main aroma.
(7) A method of imparting an aroma to a fragrance composition according to the item (6), in which the concentration of 2-isopropyl-4-methyl thiazole added to the fragrance composition is 0.1 ppm to 5,000 ppm.
(8) A method of imparting an aroma to a fragrance composition according to the item (6) or (7), in which the aroma has one or more kinds of aroma characteristics selected from freshness, sweetness, and softness.
(9) A fragrance, cosmetic, quasi drug, or goods, having blended thereto the fragrance composition according to any one of the items (1) to (5).
(10) A method of manufacturing a fragrance composition, the method including adding 2-isopropyl-4-methyl thiazole.
(11) A method of manufacturing a fragrance composition according to the item (10), in which the fragrance composition has a rose-like aroma.
(12) A method of manufacturing a fragrance composition according to the item (10) or (11), the method including adding 2-isopropyl-4-methyl thiazole and rose oxide.
(13) A method of manufacturing a fragrance composition according to any one of the items (10) to (12), in which the concentration of 2-isopropyl-4-methyl thiazole added to the fragrance composition is 6.1 ppm to 5,000 ppm.
(14) A method of manufacturing a fragrance composition according to any one of the items (10) to (13), in which the mix ratio of 2-isopropyl-4-methyl thiazole to rose oxide in the fragrance composition is in a range of 1:1 to 1:250.

Moreover, the inventors of the present invention have found that the addition of methyl epijasmonate, which has not been elucidated as an aroma component in a rose essential oil, can provide an excellent rose-like aroma with naturalness, freshness, and richness.

That is, the present invention includes the following.
(15) A rose-like fragrance composition, having added thereto methyl epijasmonate (provided that a case where a natural jasmine fragrance containing methyl epijasmonate is added alone as methyl epijasmonate is excluded).
(16) A rose-like fragrance composition according to the item (15), in which the rose-like fragrance composition has methyl epijasmonate and 2-isopropyl-4-methyl thizole added thereto.
(17) A rose-like fragrance composition according to the item (15) or (16), in which methyl epijasmonate is added to the rose-like fragrance composition at a concentration of 0.1 ppm to 1,000 ppm.
(18) A rose-like fragrance composition according to any one of the items (15) to (17), in which the mix ratio of methyl epijasmonate to 2-isopropyl-4-methyl thiazole in the rose-like fragrance composition is in the range of 100:1 to 1:500.
(19) A fragrance, cosmetic, quasi drug, or goods, having blended thereto the rose-like fragrance composition according to any one of the items (15) to (18).
(20) A method of imparting an aroma to a fragrance composition, the method including adding methyl epijasmonate to a base fragrance composition having a rose-like aroma as a main aroma (provided that a case where a natural jasmine fragrance containing methyl epijasmonate is added alone as methyl epijasmonate is excluded).
(21) A method of imparting an aroma to a fragrance composition according to the item (20), the method including adding methyl epijasmonate and 2-isopropyl-4-methyl thiazole to abase fragrance composition having a rose-like aroma as a main aroma.
(22) A method of imparting an aroma to a fragrance composition according to the item (20) or (21), in which the concentration of methyl epijasmonate added to the rose-like fragrance composition is 0.1 ppm to 1,000 ppm.
(23) A method of imparting an aroma to a fragrance composition according to any one of the items (20) to (22), in which the mix ratio of methyl epijasmonate to 2-isopropyl-4-methyl thiazole in the rose-like fragrance composition is in the range of 100:1 to 1:500.
(24) A method of imparting an aroma to a fragrance composition according to any one of the items (20) to (23), in which the aroma has one or more kinds of aroma characteristics selected from naturalness, freshness, and richness.
(25) A method of manufacturing a rose-like fragrance composition, the method including adding methyl epijasmonate (provided that a case where a natural jasmine fragrance containing methyl epijasmonate is added alone as methyl epijasmonate is excluded).
(26) A method of manufacturing a rose-like fragrance composition according to the item (25), the method including adding methyl epijasmonate and 2-isopropyl-4-methyl thiazole.
(27) A method of manufacturing a rose-like fragrance composition according to the item (25) or (26), in which the concentration of methyl epijasmonate added to the rose-like fragrance composition is 0.1 ppm to 1,000 ppm.
(28) A method of manufacturing a rose-like fragrance composition according to any one Of the items (25) to (27), in which the mix ratio of methyl epijasmonate to 2-isopropyl-4-methyl thiazole in the rose-like fragrance composition is in the range of 100:1 to 1:500.

Advantageous Effects of Invention

According to the present invention, it is possible to produce a fragrance composition having a natural aroma with freshness, sweetness, and softness by adding 2-isopropyl-4-methyl thiazole.

Further, it is possible to produce a fragrance composition having a natural aroma with freshness, sweetness, and softness at a higher level by adding 2-isopropyl-4-methyl thiazole to a base fragrance composition having a rose-like aroma as a main aroma.

Moreover, according to the present invention, it is possible to produce a fragrance composition having an aroma with naturalness, freshness, and richness by adding methyl epijasmonate.

Further, it is possible to produce a fragrance composition having an aroma with naturalness, freshness, and richness at a higher level by adding methyl epijasmonate to a base fragrance composition having a rose-like aroma as a main aroma.

DESCRIPTION OF EMBODIMENTS

Hereinafter, the present invention is described in detail.

1) Fragrance composition containing 2-isopropyl-4-methyl thiazole

A fragrance composition of the present invention is characterized by containing 2-isopropyl-4-methyl thiazole. When 2-isopropyl-4-methyl thiazole is added to a base fragrance composition, an excellent rose-like aroma can be created.

[Fragrance Component]

2-Isopropyl-4-methyl thiazole used in the present invention is a known compound and can be manufactured by a known method. Further, the compound is commercially available and can be easily obtained.

It has not been reported that this compound, i.e., 2-isopropyl-4-methyl thiazole has been discovered as a rose aroma component.

Moreover, when rose oxide is added in addition to 2-isopropyl-4-methyl thiazole, a brilliant and natural aroma of rose is more improved.

That is, the fragrance composition of the present invention more preferably contains 2-isopropyl-4-methyl thiazole and rose oxide.

Rose oxide is a known compound and can be manufactured by a known method. Further, the compound is commercially available and can be easily obtained.

[Blending Ratio]

When 2-isopropyl-4-methyl thiazole is added to a base fragrance composition, a natural aroma with freshness, sweetness, and softness can be imparted. The concentration of the compound added is, as a final concentration in the base fragrance composition, preferably 0.1 ppm to 5,000 ppm, more preferably 1 ppm to 100 ppm, particularly preferably 5 ppm to 50 ppm.

In the case where the amount of 2-isopropyl-4-methyl thiazole blended is too small, the effect of the present invention may not be exerted, while in the case where the blending amount is too large, an aroma may become ill-balanced and far from the natural aroma with freshness, sweetness, and softness of rose because its fruity aroma like mature peach or tropical fruits becomes strong.

Further, when rose oxide is further added to the fragrance composition of the present invention, a green-like or a floral-like naturalness is imparted to the aroma. The amount of rose oxide added is adjusted so that a mix ratio between 2-isopropyl-4-methyl thiazole and rose oxide in the fragrance composition is in a range of 1:1 to 1:250, more preferably 1:2 to 1:10, particularly preferably 1:3 to 1:8.

In the case where the ratio of rose oxide blended is too small, the above-mentioned effect may not be exerted, while in the case where the ratio is too large, the aroma may become ill-balanced and far from the natural aroma with freshness, sweetness, and softness of rose.

[Method of Imparting Aroma to Fragrance Composition and Method of Manufacturing the Composition]

The rose fragrance of the fragrance composition according to the present invention has a distinctive aroma including both features of a strong, passionate, and sophisticated aroma of damask rose and a graceful and elegant aroma of tea rose.

That is, in the present invention, when 2-isopropyl-4-methyl thiazole is added to the base fragrance composition having a rose-like aroma as a main aroma, more preferably, when 2-isopropyl-4-methyl thiazole and rose oxide are added thereto in combination, an aroma can be imparted to the fragrance composition. In particular, mild and natural aroma characteristics including freshness, sweetness, and softness can be imparted.

In a method of imparting an aroma to the fragrance composition of the present invention, a preferred concentration of 2-isopropyl-4-methyl thiazole added and the mix ratio between 2-isopropyl-4-methyl thiazole and rose oxide in the case of using rose oxide in combination are as mentioned above for the fragrance composition of the present invention.

It should be noted that, in the present invention, the base fragrance composition is an important part for a blended fragrance and refers to a blended fragrance which serves as a skeleton of a variety of types of aromas such as a floral aroma, a fruit aroma, a citrus aroma, and a herb aroma and is used for imparting all characters of aroma's to the fragrance composition (blended fragrance to be used for a final product).

The base fragrance composition to be used in the present invention preferably has a rose-like aroma, and examples thereof include compositions containing geraniol, citronellol, phenyl ethyl alcohol, linalool, rhodinol, geranyl acetate, citronellyl acetate, and eugenol.

Further, a method of manufacturing the fragrance composition according to the present invention is not particularly limited except that the method includes adding 2-isopropyl-4-methyl thiazole, and any usual method may be employed.

The fragrance composition of the present invention may contain a solvent such as ethanol, dipropylene glycol, diethyl phthalate, propylene glycol, triethyl citrate, benzyl benzoate, glycerin, or triacetin as long as a balance of the aroma is not lost. Moreover, if necessary, a known fragrance preparation such as a solubilizer, a stabilizer, an antioxidant, an ultraviolet absorber, or a colorant may be blended.

Another fragrance component to be used together with 2-isopropyl-4-methyl thiazole to form the fragrance composition of the present invention may be a natural fragrance or a synthetic fragrance, and examples thereof include linalool, geraniol, rose oxide, nerol, 2-phenyl ethyl alcohol, and γ-hexylactone.

Further, when 2-isopropyl-4-methyl thiazole is added to the base fragrance composition having a rose-like aroma as a main aroma, a fragrance composition having a natural aroma with freshness, sweetness, and softness at a higher level can be obtained.

The fragrance composition according to the present invention can be applied to fragrances or cosmetics including; a perfume, an eau de cologne, cosmetics such as a lotion, a milk, and a foundation; body cleansing agents such as a soap and a body soap; and hair cosmetics such as a shampoo, a conditioner, and a treatment.

Moreover, the composition may also be used for: quasi drugs such as a bath powder and a hair dye; goods such as a room deodorant, an aerosol-type deodorant, an incense stick, and a cloth; and the like.

The amount of the fragrance composition of the present invention added to the above-mentioned fragrances or cosmetics, quasi drugs, goods, or the like is not particularly limited and may be almost the same as that of a usual fragrance composition added to the various fragrances or cosmetics, quasi drugs, or goods. That is, usually, the composition may be blended (added) in an amount of about 0.001 to 100 mass % with respect to the fragrances or cosmetics, quasi drugs, or goods, or the like.

2) Fragrance Composition Containing Methyl Epijasmonate

Further, the fragrance composition of the present invention is characterized by containing methyl epijasmonate. When methyl epijasmonate is added to a base fragrance composition, an excellent rose-like aroma can be created.

[Fragrance Component]

In the present invention, "methyl epijasmonate," which is a "cis-form" of methyl jasmonate, is used. It should be noted that a general synthetic product of methyl jasmonate is in a "trans-form" in many cases (see Non Patent Literature 4).

Here, methyl epijasmonate is a compound having a cis-form structure in binding sites of two side chains on the cyclopentane ring of methyl jasmonate, and specifically refers to a compound represented by "methyl 1,2-cis-3-oxo-2α-[(Z)-2-pentenyl]-1α-cyclopentaneacetate."

Hitherto, it has not been reported that methyl epijasmonate was found in a rose aroma component.

Methyl epijasmonate is a known compound and can be manufactured by a known method.

Methyl epijasmonate to be used in the present invention may be, for example, a synthetic methyl jasmonate containing methyl epijasmonate (cis-form) at an increased content. Specifically, the content ratio of methyl epijasmonate (cis-form) is preferably 5% or more, more preferably 10% or more, still more preferably 15% or more, particularly preferably 20% or more.

In addition, such compound is commercially available and can be easily obtained. Examples of the commercially available synthetic methyl jasmonate containing methyl epijasmonate at an increased content include ZEPPIN (registered trademark) methyl epijasmonate content: 20 to 23%) "manufactured by ZEON CORPORATION." Further, a compound obtained by a known method of manufacturing a product containing epi-form methyl jasmonate at a high content (for example, see JP 2857628 B [epi-form content: 6 to 8%]) may be used.

Moreover, when 2-isopropyl-4-methyl thiazole is added in addition to methyl epijasmonate, a brilliant and natural aroma of rose is more improved.

That is, the fragrance composition of the present invention more preferably contains methyl epijasmonate and 2-isopropyl-4-methyl thiazole.

2-Isopropyl-4-methyl thiazole is a known compound and can be manufactured by a known method. Moreover, the compound is commercially available and can be easily obtained.

[Blending Ratio]

When methyl epijasmonate is added to the base fragrance composition, naturalness, freshness, and richness is imparted to the aroma.

The amount of methyl epijasmonate added is adjusted so that the concentration of methyl epijasmonate added to the fragrance composition is preferably 0.1 ppm to 1,000 ppm, more preferably 0.2 ppm to 200 ppm, particularly preferably 2 ppm to 20 ppm. In the case where the blending amount is too small, the effect of the present invention may not be exerted, while in the case where the blending amount is too large, the aroma may become ill-balanced and far from the natural, fresh, and rich aroma of rose.

In addition, when 2-isopropyl-4-methyl thiazole is further added to the fragrance composition of the present invention, naturalness with freshness, sweetness, and softness of rose is further imparted to the aroma. The amount of 2-isopropyl-4-methyl thiazole added is adjusted so that the mix ratio between methyl epijasmonate and 2-isopropyl-4-methyl thiazole in the fragrance composition is preferably in a range of 100:1 to 1:500, more preferably in a range of 10:1 to 1:10, particularly preferably 2:1 to 1:5.

In the case where the amount of 2-isopropyl-4-methyl thiazole blended is too small, the above-mentioned effect may not be exerted, while in the case where the amount is too large, the aroma may become ill-balanced and far from the natural, fresh, and rich aroma of rose.

[Method of Imparting Aroma to Fragrance Composition and Method of Manufacturing the Composition]

In the present invention, when methyl epijasmonate is added to the base fragrance composition having a rose-like aroma as a main aroma, more preferably, when methyl epijasmonate and 2-isopropyl-4-methyl thiazole are added thereto in combination, an aroma can be imparted to the fragrance composition. In particular, a mild aroma such as the natural, fresh, and rich aroma can be imparted.

In the method of imparting an aroma to the fragrance composition of the present invention, a preferred concentration of methyl epijasmonate added and the mix ratio between methyl epijasmonate and 2-isopropyl-4-methyl thiazole in the case of using 2-isopropyl-4-methyl thiazole in combination are as mentioned above for the fragrance composition of the present invention.

It should be noted that, in the present invention, the base fragrance composition is an important part for a blended fragrance and refers to a blended fragrance which serves as a skeleton of a variety of types of aromas such as a floral aroma, a fruit aroma, a citrus aroma, and a herb aroma and is used for imparting all characters of aromas to the fragrance composition (blended fragrance to be used for a final product).

The base fragrance composition to be used in the present invention preferably has a rose-like aroma, and examples thereof include compositions containing geraniol, citronellol, phenyl ethyl alcohol, linalool, rhodinol, geranyl acetate, citronellyl acetate, and eugenol.

Further, a method of manufacturing the fragrance composition according to the present invention is not particularly limited except that the method includes adding methyl epijasmonate, and any usual method may be employed.

The fragrance composition of the present invention may contain a solvent such as ethanol, dipropylene glycol, diethyl phthalate, propylene glycol, triethyl citrate, benzyl benzoate, glycerin, or triacetin as long as a balance of the aroma is not lost. Moreover, if necessary, a known fragrance preparation such as a solubilizer, a stabilizer, an antioxidant, an ultraviolet absorber, or a colorant may be blended.

Another fragrance component to be used together with the above-mentioned methyl epijasmonate and 2-isopropyl-4-methyl thiazole to manufacture the fragrance composition of the present invention may be a natural fragrance or a synthetic fragrance, and examples thereof include linalool, geraniol, rose oxide, nerol, 2-phenyl ethyl alcohol, and γ-hexylactone.

Further, when methyl epijasmonate is added to the base fragrance composition having a rose-like aroma as a main aroma, a fragrance composition having an aroma with naturalness, freshness, and richness at a higher level can be obtained.

[Products]

The fragrance composition according to the present invention can be applied to fragrances or cosmetics including; a perfume, an eau de cologne, cosmetics such as a lotion, a milky lotion, and a foundation; body cleansing agents such as a soap and a body soap; and hair cosmetics such as a shampoo, a conditioner, and a treatment.

Moreover, the composition may be used for: quasi drugs such as a bath powder and a hair dye; goods such as a room deodorant, an aerosol-type deodorant, an incense stick, and a cloth; and the like.

The amount of the fragrance composition of the present invention added to the above-mentioned fragrances or cosmetics, quasi drugs, goods, or the like is not particularly limited and may be almost the same as that of a usual fragrance composition added to the various fragrances or cosmetics, quasi drugs, or goods. That is, usually, the composition may be blended (added) in an amount of about 0.001 to 100 mass % with respect to the fragrances or cosmetics, quasi drugs, goods, or the like.

EXAMPLES

The present invention is described below in detail by way of examples. However, the present invention is not limited by the examples. Blending amounts are expressed in terms of parts by mass unless otherwise specified.

Example 1

Fragrance composition containing 2-isopropyl-4-methyl thiazole

Test Example 1-1

Test on effect of 2-isopropyl-4-methyl thiazole (1) Rose-Like Base Fragrance Composition According to the following formulation, a rose-like base fragrance composition was prepared by a conventional method.

Formulation Example 1-1

| (Components) | Parts by mass |
| --- | --- |
| Geraniol | 355.0 |
| Citronellol | 260.0 |
| Phenyl ethyl alcohol | 150.0 |
| Linalool | 80.0 |
| Rhodinol | 60.0 |
| Geranyl acetate | 35.0 |
| Citronellyl acetate | 30.0 |
| Eugenol | 30.0 |
| Total | 1,000.0 |

(2) Evaluation of Aroma

2-Isopropyl-4-methyl thiazole was added to the base fragrance composition of Formulation Example 1-1 at final concentrations shown in Table 1 to prepare Test Examples 1-1-1 to 1-1-10, and their aromas were evaluated. Table 1 shows mean values of the results of evaluation.

It should be noted that the aroma was evaluated by three trained panelists based on the following evaluation criteria.

4: Having a very excellent rose-like natural aroma
3: Having an excellent rose-like natural aroma
2: Having a rose-like natural aroma
1: Having little rose-like aroma

TABLE 1

| | Test Example | | | | |
| --- | --- | --- | --- | --- | --- |
| Component | 1-1-1 | 1-1-2 | 1-1-3 | 1-1-4 | 1-1-5 |
| Composition of Formulation Example 1-1 | 100 | 100 | 100 | 100 | 100 |
| 2-Isopropyl-4-methyl thiazole | 0 | 0.1 ppm | 1 ppm | 5 ppm | 30 ppm |
| Evaluation of aroma | 1.0 | 2.0 | 2.5 | 3.0 | 3.0 |

| | Test Example | | | | |
| --- | --- | --- | --- | --- | --- |
| | 1-1-6 | 1-1-7 | 1-1-8 | 1-1-9 | 1-1-10 |
| Composition of Formulation Example 1-1 | 100 | 100 | 100 | 100 | 100 |
| 2-Isopropyl-4-methyl thiazole | 50 ppm | 100 ppm | 1,000 ppm | 5,000 ppm | 1% |
| Evaluation of aroma | 3.0 | 2.5 | 2.5 | 2.0 | 1.0 |

As is clear from Table 1, in order to create a rose-like aroma, 2-isopropyl-4-methyl thiazole is added to the base fragrance composition at a final concentration of preferably 0.1 ppm to 5,000 ppm, more preferably 1 to 1,000 ppm, particularly preferably 5 ppm to 50 ppm.

Test Example 1-2

Test on Effect of Rose Oxide

Rose oxide was blended in the base fragrance composition of Formulation Example 1-1 at final concentrations shown in Table 2 to prepare Test Examples 1-2-1 to 1-2-7, and their aromas were evaluated in the same way as in Test Example 1-1. Table 2 shows mean values of the results of evaluation.

TABLE 2

| Component | Test Example | | | | | | |
|---|---|---|---|---|---|---|---|
| | 1-2-1 | 1-2-2 | 1-2-3 | 1-2-4 | 1-2-5 | 1-2-6 | 1-2-7 |
| Composition of Formulation Example 1-1 | 100 | 100 | 100 | 100 | 100 | 100 | 100 |
| Rose oxide | 0 | 5 ppm | 50 ppm | 250 ppm | 500 ppm | 5,000 ppm | 10,000 ppm |
| Evaluation of aroma | 1.0 | 2.0 | 2.3 | 2.5 | 2.3 | 2.0 | 1.0 |

As is clear from Table 2, in order to create a rose-like aroma, rose oxide is added to the base fragrance composition at a final concentration of preferably 5 ppm to 5,000 ppm, more preferably 50 ppm to 500 ppm.

Test Example 1-3

Test on effect of combination use of 2-isopropyl-4-methyl thiazole and rose oxide 2-Isopropyl-4-methyl thiazole and rose oxide were blended in the base fragrance composition of Formulation Example 1-1 at final concentrations shown in Table 3 to prepare Test Examples 1-3-1 to 1-3-10, and their aromas were evaluated in the same way as in Test Example 1-1. Table 3 shows mean values of the results of evaluation.

TABLE 3

| Sample | Test Example | | | | |
|---|---|---|---|---|---|
| | 1-3-1 | 1-3-2 | 1-3-3 | 1-3-4 | 1-3-5 |
| Composition of Formulation Example 1-1 | 100 | 100 | 100 | 100 | 100 |
| 2-Isopropyl-4-methyl thiazole | 0.5 ppm | 0.5 ppm | 0.5 ppm | 0.5 ppm | 0.5 ppm |
| Rose oxide | 0 ppm | 0.5 ppm | 1.0 ppm | 1.5 ppm | 2.5 ppm |
| Mix ratio# | — | 1:1 | 1:2 | 1:3 | 1:5 |
| Evaluation of aroma | 3.0 | 3.5 | 3.75 | 4.0 | 4.0 |

| Sample | Test Example | | | | |
|---|---|---|---|---|---|
| | 1-3-6 | 1-3-7 | 1-3-8 | 1-3-9 | 1-3-10 |
| Composition of Formulation Example 1-1 | 100 | 100 | 100 | 100 | 100 |
| 2-Isopropyl-4-methyl thiazole | 0.5 ppm | 0.5 ppm | 0.5 ppm | 0.5 ppm | 0.5 ppm |
| Rose oxide | 4 ppm | 5 ppm | 125 ppm | 250 ppm | 500 ppm |
| Mix ratio# | 1:8 | 1:10 | 1:250 | 1:500 | 1:1,000 |
| Evaluation of aroma | 4.0 | 3.75 | 3.5 | 3.0 | 2.5 |

The mix ratio between 2-isopropyl-4-methyl thiazole and rose oxide

As is clear from Table 3, the mix ratio between 2-isopropyl-4-methyl thiazole and rose oxide is preferably 1:1 to 1:250, more preferably 1:2 to 1:10., particularly preferably 1:3 to 1:8, at which a rose-like aroma is created.

Test Example 1-4

Comparison between effect of 2-isopropyl-4-methyl thiazole and effect of 2-methyl thiazole (1) Rose-Like Base Fragrance Composition According to the following formulation, a rose-like base fragrance composition was prepared.

Formulation Example 1-2

| (Components) | Parts by mass |
|---|---|
| Geraniol | 340.0 |
| Citronellol | 245.0 |
| Phenyl ethyl alcohol | 123.0 |
| Linalool | 70.0 |
| Rhodinol | 50.0 |
| Geranyl acetate | 30.0 |
| Citronellyl acetate | 25.0 |
| Eugenol | 25.0 |
| β-damascone (10% DPG solution) | 2.0 |
| α-ionone | 15.0 |
| Benzyl acetate | 12.0 |
| Benzyl alcohol | 10.0 |
| Phenyl acetaldehyde | 10.0 |
| Rose oil | 1.0 |
| Citral | 15.0 |
| Phenyl ethyl acetate | 7.0 |
| β-caryophyllene | 5.0 |
| Methyl phenyl acetate | 3.0 |
| Citronellal | 30.0 |
| Total | 1,018.0 |

(2) Evaluation of Aroma

A 1% solution of 2-isopropyl-4-methyl thiazole (solvent: dipropylene glycol (DPG)) and a 1% solution of 2-methyl thiazole (solvent: DPG) were each blended in the base fragrance composition of Formulation Example 1-2 at a ratio shown in Table 4 to prepare. Sample B and Sample C, respectively, and DPG was blended instead of thiazole at a ratio shown in Table 4 to prepare Sample A (control).

Sample A was used as a control, and Sample B containing 0.005% 2-isopropyl-4-methyl thiazole was compared with Sample C containing 0.005% 2-methyl thiazole to evaluate their aromas by seven trained panelists based on the following evaluation criteria. Table 4 shows mean values of the results of evaluation.

5: Having imparted thereto a very excellent natural, fresh, and rich aroma.
4: Having imparted thereto an excellent natural, fresh, and rich aroma.
3: Having imparted thereto a slightly excellent natural, fresh, and rich aroma.
2: Having imparted thereto a natural, fresh, and rich aroma. 1: No effect.

TABLE 4

| Component | Sample A | Sample B | Sample C |
|---|---|---|---|
| Composition of Formulation Example 1-2 | 995 | 995 | 995 |
| Dipropylene glycol (DPG) | 5 | — | — |
| 2-Isopropyl-4-methyl thiazole (1% DPG solution) | — | 5 | — |
| 2-Methyl thiazole (1% DPG solution) | — | — | 5 |
| Evaluation of aroma | 1.0 | 4.9 | 2.6 |

As is clear from Table 4, Sample B prepared by blending 2-isopropyl-4-methyl thiazole was found to have a very excellent natural, fresh, and rich aroma. On the other hand, Sample C prepared by blending 2-methyl thiazole was found to have a natural, fresh, and rich aroma, but the level of the aroma was much lower than that of Sample B.

Test Example 1-5

Stability Test

The fragrance composition of Test Example 1-3-5 was dissolved in 95% ethyl alcohol at a concentration of 5% and stored at 0° C. and 40° C. separately for three months, and stability of the aromas of the solution was examined.

As a result, the fragrance compositions containing 2-isopropyl-4-methyl thiazole and rose oxide, stored at 40° C. and 0° C., were compared with the fragrance composition immediately after dissolution, but the compositions were found not to change in their aromas and to keep their good aromas.

Production Example 1-1

Lotion

According to the following formulation, a lotion was prepared by a conventional method.

| (Blending components) | (mass %) |
|---|---|
| Ethyl alcohol | 5 |
| Glycerin | 1 |
| 1,3-Butylene glycol | 5 |
| Polyoxyethylene polyoxypropylene decyl tetradecyl ether | 0.2 |
| Sodium hexametaphosphate | 0.03 |
| Trimethylglycine | 1 |
| Sodium polyaspartate | 0.1 |
| Potassium α-tocopherol 2-L-ascorbate phosphate diester | 0.1 |
| Thiotaurine | 0.1 |
| Iris Florentina Root Extract | 0.1 |
| Trisodium EDTA | 0.1 |
| Carboxyvinyl polymer | 0.05 |
| Potassium hydroxide | 0.02 |
| Phenoxyethanol | q.s |
| "Test Example 1-3-5" | 0.01 |
| Purified water | Balance |

Production Example 1-2

Cream

According to the following formulation, a cream was prepared by a conventional method.

| (Blending components) | (mass %) |
|---|---|
| Stearic acid | 10.0 |
| Stearyl alcohol | 4.0 |
| Butyl stearate | 8.0 |
| Monoglycerin stearate | 2.0 |
| Vitamin E acetate | 0.5 |
| Vitamin A palmitate | 0.1 |
| Macadamia nut oil | 1.0 |
| Tea seed oil | 3.0 |
| Glycerin | 4.0 |
| 1,2-Pentanediol | 3.0 |
| Sodium hyaluronate | 1.0 |
| Potassium hydroxide | 2.0 |
| Ascorbic acid glucoside | 2.0 |

-continued

| (Blending components) | (mass %) |
|---|---|
| L-arginine hydrochloride | 0.01 |
| Trisodium edetate | 0.05 |
| Fragrance composition of "Test Example 1-3-5" | 0.1 |
| Preservative | q.s. |
| Purified water | Balance |

Production Example 1-3

Milky Lotion

According to the following formulation, a milky lotion was prepared by a conventional method.

| (Blending Components) | (mass %) |
|---|---|
| Squalene | 5.0 |
| Oleyl oleate | 3.0 |
| Petrolatum | 2.0 |
| Sorbitan sesquioleate | 0.8 |
| POE(20) oleyl ether | 1.2 |
| Evening primrose oil | 0.5 |
| 1,3-Butylene glycol | 4.5 |
| Ethanol | 3.0 |
| Carboxyvinyl polymer | 0.2 |
| Potassium hydroxide | 0.1 |
| L-arginine L-aspartate salt | 0.01 |
| Edetic acid salt | 0.05 |
| Fragrance composition of "Test Example 1-3-5" | 0.05 |
| Preservative | q.s. |
| Purified water | Balance |

Production Example 1-4

Hair Treatment

The following components were mixed in accordance with a conventional method, to thereby prepare a hair treatment.

| (Blending components) | (mass %) |
|---|---|
| Dimethylpolysiloxane (20 cs) | 10.0 |
| Stearyl dihidroxypropyl dimonium oligosaccharide | 1.2 |
| Hydroxyethyl urea | 0.4 |
| Octyl palmitate | 0.3 |
| Citric acid | q.s. |
| Cetanol | 1.0 |
| Hardened rapeseed oil alcohol | 4.5 |
| Behentrimethylammonium chloride | 3.0 |
| Sodium benzoate | q.s. |
| Glycerin | 22.0 |
| Isoprene glycol | 10.0 |
| Fragrance composition of "Test Example 1-3-5" | 0.5 |
| Purified water | Balance |

Production Example 1-5

Hair Shampoo

The following components were mixed in accordance with a conventional method, to thereby prepare a hair shampoo.

| (Blending components) | (mass %) |
|---|---|
| POE lauryl sulfate triethanolamine salt | 10.0 |
| Lauric acid diethanolamide | 1.0 |
| Lauryldimethylaminoacetate betaine | 5.0 |
| Ethylene glycol distearate | 3.0 |
| Propylene glycol | 2.0 |
| Sodium benzoate | 0.5 |
| Hydroxyethyl urea | 10.0 |
| Lactic acid | 0.4 |
| Ammonium lactate | 0.2 |
| Coloring material | q.s. |
| Fragrance composition of "Test Example 1-3-5" | 0.5 |
| Purified water | Balance |

Production Example 1-6

Bath Preparation

According to the following formulation, a bath preparation was prepared. That is, the following components excluding the fragrance composition were stirred using a V-shaped mixer to homogenize them, and the fragrance composition was added thereto, followed by stirring well to homogenize them, to thereby obtain a bath preparation.

| (Blending components) | (mass %) |
|---|---|
| Sodium hydrogen carbonate | 70.0 |
| Anhydrous sodium sulfate | 28.8 |
| Fragrance composition of "Test Example 1-3-5" | 1.0 |
| Pigment Y-202-1 | 0.2 |

Production Example 1-7

Gel Deodorant

According to the following formulation, a gel deodorant was prepared. That is, carrageenan, propylene glycol, and propylparaben were mixed, and ion-exchanged water was added thereto with stirring. The mixture was heated to about 80° C. with gentle stirring. Thereafter, the mixture was cooled to about 65° C., and the fragrance composition was added thereto with stirring at 3,000 rpm using a homogenizer to prepare a homogeneous phase. The mixture was poured into a predetermined container and allowed to cool naturally, to thereby prepare a deodorant.

| (Blending components) | (mass %) |
|---|---|
| Carrageenan | 3.0 |
| Propylene glycol | 2.0 |
| Propylparaben | 0.3 |
| Fragrance composition of "Test Example 1-3-5" | 5.0 |
| Ion-exchanged water | 89.7 |

Example 2

Fragrance Composition Containing Methyl Epijasmonate

Test Example 2-1

Test on Effect of Methyl Epijasmonate (1) Rose-Like Base Fragrance Composition According to the following formulation, a rose-like base fragrance composition was prepared by a conventional method.

Formulation Example 2-1

| (Components) | parts by mass |
|---|---|
| Geraniol | 550.00 |
| Nerol | 100.00 |
| Citral | 90.00 |
| Dimethoxymethylbenzene | 65.00 |
| L-citronellol | 65.00 |
| Dihydro-β-ionol | 60.00 |
| Geranyl acetate | 35.00 |
| Dihydro-β-ionone | 10.00 |
| Farnesol | 5.00 |
| Methyl geranate | 5.00 |
| L-citronellyl acetate | 4.00 |
| Indole | 0.80 |
| Theaspirane | 0.50 |
| Dipropylene glycol | 4.70 |
| Total | 995.00 |

(2) Evaluation of Aroma

To 995 parts of the base fragrance composition of Formulation Example 2-1 were added 5 parts each of dipropylene glycol (DPG) alone as a solvent (Sample A), of 1% DPG solution of methyl epijasmonate-rich methyl jasmonate ("ZEPPIN"* manufactured by ZEON CORPORATION) (Sample B), of 1% DPG solution of methyl jasmonate (product manufactured by File Monnig S. A.) (Sample C), and of 1% DPG solution of jasmine absolute (Sample D), and the aroma of the resultant was evaluated. Table 5 shows mean values of the results of evaluation.

*Methyl jasmonate containing 20 to 23% of methyl epijasmonate (ZEON CORPORATION, catalog 2008, p. 44)

It should be noted that the aromas were evaluated by seven trained panelists based on the following evaluation criteria.

5: Having imparted thereto a very excellent rose-like natural, fresh, and rich aroma.

4: Having imparted thereto an excellent rose-like natural, fresh, and rich aroma.

3: Having imparted thereto a slightly excellent rose-like natural, fresh, and rich aroma.

2: Having imparted thereto a rose-like natural, fresh, and rich aroma.

1: No effect.

TABLE 5

| Sample | A Only DPG | B Methyl epijasmonate-rich DPG | C Methyl jasmonate-containing DPG | D Jasmine absolute-containing DPG |
|---|---|---|---|---|
| Evaluation of aroma | 1.0 | 4.8 | 2.5 | 3.0 |

As is clear from Table 5, Sample B prepared by adding methyl epijasmonate to the rose-like base fragrance composition at a high concentration was found to have a very excellent rose-like natural, fresh, and rich aroma.

On the other hand, Sample C prepared by blending methyl jasmonate having a similar chemical structure was found to have an insufficient fresh and rich aroma and to lack in attractive fragrance.

Moreover, Sample D prepared by blending jasmine absolute, which is known to contain methyl epijasmonate at a small amount, imparted a floral, rich, and voluminous fragrance but was found to have insufficient effect of imparting a rose-like aroma.

Test Example 2-2

Test on Effect of Methyl Epijasmonate (1) Rose-Like Base Fragrance Composition

According to the following formulation, a rose-like base fragrance composition was prepared by a conventional method.

Formulation Example 2-2

| (Components) | parts by mass |
|---|---|
| Geraniol | 550.00 |
| Nerol | 100.00 |
| Citral | 90.00 |
| Dimethoxymethylbenzene | 65.00 |
| L-citronellol | 65.00 |
| Dihydro-β-ionol | 60.00 |
| Geranyl acetate | 35.00 |
| Dihydro-β-ionone | 10.00 |
| Farnesol | 5.00 |
| Methyl geranate | 5.00 |
| L-citronellyl acetate | 4.00 |
| Indole | 0.80 |
| Theaspirane | 0.50 |
| Dipropylene glycol | 9.70 |
| Total | 1,000.00 |

(2) Evaluation of Aroma

Methyl jasmonate containing methyl epijasmonate at a high concentration ("ZEPPIN*" manufactured by ZEON CORPORATION) was added to the base fragrance composition of Formulation Example 2-2 so that methyl epijasmonate was contained at final concentrations shown in Table 6 to prepare Test Examples 2-2-1 to 2-2-12, and their aromas were evaluated. Table 6 shows mean values of the results of evaluation.

*Methyl jasmonate containing 20 to 23% methyl epijasmonate (ZEON CORPORATION, catalog 2008, p. 44)

It should be noted that the aromas were evaluated by seven trained panelists based on the following evaluation criteria.

5: Having imparted thereto a very excellent rose-like natural, fresh, and rich aroma.

4: Having imparted thereto an excellent rose-like natural, fresh, and rich aroma.

3: Having imparted thereto a slightly excellent rose-like natural, fresh, and rich aroma.

2: Having imparted thereto a rose-like natural, fresh, and rich aroma.

1: No effect.

TABLE 6

| | Test Example | | | | | |
|---|---|---|---|---|---|---|
| Sample | 2-2-1 | 2-2-2 | 2-2-3 | 2-2-4 | 2-2-5 | 2-2-6 |
| "ZEPPIN" (epi-form content*) | 0 (0) | 0.1 ppm (0.02 ppm) | 0.5 ppm (0.1 ppm) | 1.0 ppm (0.2 ppm) | 5 ppm (1 ppm) | 10 ppm (2 ppm) |
| Evaluation of aroma | 1.0 | 1.5 | 2.0 | 3.0 | 3.5 | 4.0 |

| | Test Example | | | | | |
|---|---|---|---|---|---|---|
| Sample | 2-2-7 | 2-2-8 | 2-2-9 | 2-2-10 | 2-2-11 | 2-2-12 |
| "ZEPPIN" (epi-form content*) | 50 ppm (10 ppm) | 100 ppm (20 ppm) | 500 ppm (100 ppm) | 1,000 ppm (200 ppm) | 5,000 ppm (1,000 ppm) | 1% (0.2%) |
| Evaluation of aroma | 5.0 | 4.0 | 3.5 | 3.5 | 2.5 | 1.0 |

*An epi-form content (final concentration) calculated on the assumption that the methyl epijasmonate content in "ZEPPIN" is 20%.

As is clear from Table 6, in order to create a rose-like aroma, methyl epijasmonate is added to the base fragrance composition at a concentration of preferably 0.1 ppm to 1,000 ppm, more preferably 0.2 to 200 ppm, particularly preferably 2 ppm to 20 ppm.

Test Example 2-3

Test on effect of combination use of methyl epijasmonate and 2-isopropyl-4-methyl thiazole Methyl jasmonate containing methyl epijasmonate at a high concentration ("ZEPPIN*" manufactured by ZEON CORPORATION) and 2-isopropyl-4-methyl thiazole were blended in the base fragrance composition of Formulation Example 2-2 at final concentrations shown in Table 7 to prepare Test Examples 2-3-1 to 2-3-10, and their aromas were evaluated in the same way as in Test Example 2-1. Table 7 shows mean values of the results of evaluation.
*Methyl jasmonate containing 20 to 23% methyl epijasmonate (ZEON CORPORATION, catalog 2008, p. 44)

It should be noted that the aromas were evaluated by seven trained panelists based on the following evaluation criteria in which the evaluation for Test Example 2-3-1, which has the same formulation as that of Test Example 2-2-7, was defined as 5.
9: Having imparted thereto a very excellent rose-like natural, fresh, and rich aroma.
8: Having imparted thereto an excellent rose-like natural, fresh, and rich aroma.
7: Having imparted thereto a slightly excellent rose-like natural, fresh, and rich aroma.
6: Having imparted thereto a rose-like natural, fresh, and rich aroma.
5: No effect. (equivalent to the highest evaluation in Test Example 2-2)

TABLE 7

| Sample | Test Example | | | | |
|---|---|---|---|---|---|
|  | 2-3-1 | 2-3-2 | 2-3-3 | 2-3-4 | 2-3-5 |
| "ZEPPIN" | 50 ppm | 50 ppm | 50 ppm | 50 ppm | 50 ppm |
| (epi-form content*) | (10 ppm) | (10 ppm) | (10 ppm) | (10 ppm) | (10 ppm) |
| 2-Isopropyl-4-methyl thiazole | 0 | 0.1 ppm | 1 ppm | 5 ppm | 30 ppm |
| Mix ratio# | — | 100:1 | 10:1 | 2:1 | 1:3 |
| Evaluation of aroma | 5.0 | 6.0 | 7.0 | 8.5 | 9.0 |

| Sample | Test Example | | | | |
|---|---|---|---|---|---|
|  | 2-3-6 | 2-3-7 | 2-3-8 | 2-3-9 | 2-3-10 |
| "ZEPPIN" | 50 ppm | 50 ppm | 50 ppm | 50 ppm | 50 ppm |
| (epi-form content*) | (10 ppm) | (10 ppm) | (10 ppm) | (10 ppm) | (10 ppm) |
| 2-Isopropyl-4-methyl thiazole | 50 ppm | 100 ppm | 1,000 ppm | 5,000 ppm | 1% |
| Mix ratio# | 1:5 | 1:10 | 1:100 | 1:500 | 1:1,000 |
| Evaluation of aroma | 9.0 | 7.0 | 6.0 | 6.0 | 5.0 |

*An epi-form content (final concentration) calculated on the assumption that the methyl epijasmonate content in "ZEPPIN" is 20%.
The mix ratio between methyl epijasmonate and 2-isopropyl-4-methyl thiazole As is clear from Table 7, the mix ratio between methyl epijasmonate and 2-isopropyl-4-methyl thiazole is preferably 100:1 to 1:500, more preferably 10:1 to 1:10, particularly preferably 2:1 to 1:5, at which a very excellent rose-like natural, fresh, and rich aroma is imparted.

Test Example 2-4

Stability Test

The fragrance composition of Test Example 2-3-6 was dissolved in 95% ethyl alcohol at a concentration of 5%, and stability of the aroma of the solution was examined after the solution was stored at 0° C. or 40° C. for three months.

As a result, the fragrance of the solution containing methyl epijasmonate did not significantly change, and the good fragrance was maintained.

Production Example 2-1

Lotion

A lotion was prepared by a conventional method except that the following formulation was used.

| (Blending components) | (mass %) |
|---|---|
| Ethyl alcohol | 5 |
| Glycerin | 1 |
| 1,3-Butylene glycol | 5 |
| Polyoxyethylene polyoxypropylene decyl tetradecyl ether | 0.2 |
| Sodium hexametaphosphate | 0.03 |
| Trimethylglycine | 1 |
| Sodium polyaspartate | 0.1 |
| Potassium α-tocopherol 2-L-ascorbate phosphate diester | 0.1 |
| Thiotaurine | 0.1 |
| *Iris Florentina* Root Extract | 0.1 |
| Trisodium EDTA | 0.1 |
| Carboxyvinyl polymer | 0.05 |
| Potassium hydroxide | 0.02 |
| Phenoxyethanol | q.s. |
| Purified water | Balance |
| Fragrance composition of "Test Example 2-3-6" | 0.01 |

Production Example 2-2

Cream

A cream was prepared by a conventional method except that the following formulation was used.

| (Blending components) | (mass %) |
| --- | --- |
| Stearic acid | 10.0 |
| Stearyl alcohol | 4.0 |
| Butyl stearate | 8.0 |
| Monoglycerin stearate | 2.0 |
| Vitamin E acetate | 0.5 |
| Vitamin A palmitate | 0.1 |
| Macadamia nut oil | 1.0 |
| Tea seed oil | 3.0 |
| Glycerin | 4.0 |
| 1,2-Pentanediol | 3.0 |
| Sodium hyaluronate | 1.0 |
| Potassium hydroxide | 2.0 |
| Ascorbic acid glucoside | 2.0 |
| L-arginine hydrochloride | 0.01 |
| Trisodium edetate | 0.05 |
| Fragrance composition of "Test Example 2-3-6" | 0.1 |
| Preservative | q.s. |
| Purified water | Balance |

Production Example 2-3

Milky Lotion

A milky lotion was prepared by a conventional method except that the following formulation was used.

| (Blending Components) | (mass %) |
| --- | --- |
| Squalene | 5.0 |
| Oleyl oleate | 3.0 |
| Petrolatum | 2.0 |
| Sorbitan sesquioleate | 0.8 |
| POE(20) oleyl ether | 1.2 |
| Evening primrose oil | 0.5 |
| 1,3-Butylene glycol | 4.5 |
| Ethanol | 3.0 |
| Carboxyvinyl polymer | 0.2 |
| Potassium hydroxide | 0.1 |
| L-arginine L-aspartate salt | 0.01 |
| Edetic acid salt | 0.05 |
| Fragrance composition of "Test Example 2-3-6" | 0.05 |
| Preservative | q.s. |
| Purified water | Balance |

Production Example 2-4

Hair Shampoo

A hair shampoo was prepared by a conventional method except that the following formulation was used.

| (Blending components) | (mass %) |
| --- | --- |
| POE lauryl sulfate triethanolamine salt | 10.0 |
| Lauric acid diethanolamide | 1.0 |
| Lauryldimethylaminoacetate betaine | 5.0 |
| Ethylene glycol distearate | 3.0 |
| Propylene glycol | 2.0 |
| Sodium benzoate | 0.5 |
| Hydroxyethyl urea | 10.0 |
| Lactic acid | 0.4 |
| Ammonium lactate | 0.2 |
| Coloring material | q.s. |
| Fragrance composition of "Test Example 2-3-6" | 0.5 |
| Purified water | Balance |

Production Example 2-5

Bath Preparation

First, the following components excluding the fragrance (fragrance composition) were stirred using a V-shaped mixer to homogenize them, and the following fragrance (fragrance composition) was added thereto, followed by stirring well to homogenize them, to thereby obtain a bath preparation.

| (Blending components) | (mass %) |
| --- | --- |
| Sodium hydrogen carbonate | 70.0 |
| Anhydrous sodium sulfate | 28.8 |
| Fragrance composition of "Test Example 2-3-6" | 1.0 |
| Pigment Y-202-1 | 0.2 |

Production Example 2-6

Gel Deodorant

According to the following formulation, carrageenan, propylene glycol, and propylparaben were mixed, and ion-exchanged water was added thereto with stirring. The mixture was heated to about 80° C. with gentle stirring. Thereafter, the mixture was cooled to about 65° C., and the following fragrance (fragrance composition) was added thereto with stirring at 3,000 rpm using a homogenizer to prepare a homogeneous phase. The mixture was poured into a predetermined container and allowed to cool naturally, to thereby prepare a deodorant.

| (Blending components) | (mass %) |
| --- | --- |
| Carrageenan | 3.0 |
| Propylene glycol | 2.0 |
| Propylparaben | 0.3 |
| Fragrance composition of "Test Example 2-3-6" | 5.0 |
| Ion-exchanged water | 89.7 |

INDUSTRIAL APPLICABILITY

According to the present invention, the fragrance composition having a highly-palatable, rose-like, and excellent aroma can be obtained.

The fragrance composition of the present invention can be used for: fragrances or cosmetics such as perfumes, cosmetics, body cleansing agents, and hair cosmetics; quasi drugs such as bath powders and hair dyes; and goods such as room deodorants, incense sticks, and clothes; and the like, to thereby improve the taste.

The invention claimed is:

1. A rose fragrance composition, comprising a base fragrance composition with a rose aroma and methyl epijasmonate, provided that a natural jasmine fragrance containing methyl epijasmonate as the only source of methyl epijasmonate is excluded, wherein the methyl epijasmonate is contained in the rose fragrance composition in a concentration of 0.2 ppm to 200 ppm.

2. The rose fragrance composition according to claim 1, wherein the rose fragrance composition further comprises 2-isopropyl-4-methyl thiazole.

3. The rose fragrance composition according to claim 2, wherein a mix mass ratio of the methyl epijasmonate to the 2-isopropyl-4-methyl thiazole in the rose fragrance composition is in a range of 100:1 to 1:500.

4. In a product including a fragrance, a cosmetic, a quasi drug, or goods, the improvement comprising the inclusion in the product of the rose fragrance composition according to claim 1 or 2.

5. A method of imparting an aroma to a fragrance composition, the method comprising adding methyl epijasmonate to a base fragrance composition having a rose aroma as a main aroma, provided that a natural jasmine fragrance containing methyl epijasmonate as the only source of methyl epijasmonate is excluded, wherein the methyl epijasmonate is contained in the base fragrance composition in a concentration of 0.2 ppm to 200 ppm.

6. The method of imparting an aroma to a fragrance composition according to claim 5, further comprising adding 2-isopropyl-4-methyl thiazole to the base fragrance composition.

7. The method of imparting an aroma to a fragrance composition according to claim 6, wherein a mix mass ratio of the methyl epijasmonate to the 2-isopropyl-4-methyl thiazole in the fragrance composition is in a range of 100:1 to 1:500.

8. The method of imparting an aroma to a fragrance composition according to claim 5 or 6, wherein the aroma is one or more kinds of aroma characteristics selected from the group consisting of naturalness, freshness, and richness.

9. A method of manufacturing a rose fragrance composition, the method comprising adding methyl epijasmonate to a base fragrance, provided that a natural jasmine fragrance containing methyl epijasmonate as the only source of methyl epijasmonate is excluded, wherein the methyl epijasmonate is contained in the rose fragrance composition in a concentration of 0.2 ppm to 200 ppm.

10. A method of manufacturing a rose fragrance composition according to claim 9, further comprising adding 2-isopropyl-4-methyl thiazole to the base fragrance.

11. The method of manufacturing a rose fragrance composition according to claim 10, wherein a mix mass ratio of methyl epijasmonate to 2-isopropyl-4-methyl thiazole in the rose fragrance composition is in a range of 100:1 to 1:500.

* * * * *